(12) United States Patent
Bernotas et al.

(10) Patent No.: US 7,589,108 B2
(45) Date of Patent: Sep. 15, 2009

(54) 1-HETEROCYCLYLALKYL-3-SULFONYLINDOLE OR -INDAZOLE DERIVATIVES AS 5-HYDROXYTRYPTAMINE-6 LIGANDS

(75) Inventors: Ronald Charles Bernotas, Royersford, PA (US); Steven Edward Lenicek, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 568 days.

(21) Appl. No.: 11/238,246

(22) Filed: Sep. 29, 2005

(65) Prior Publication Data

US 2006/0030593 A1 Feb. 9, 2006

Related U.S. Application Data

(62) Division of application No. 10/621,698, filed on Jul. 17, 2003, now Pat. No. 6,995,176.

(60) Provisional application No. 60/396,958, filed on Jul. 18, 2002.

(51) Int. Cl.
*A61K 31/454* (2006.01)
*C07D 403/02* (2006.01)
(52) U.S. Cl. ............... 514/322; 546/199
(58) Field of Classification Search .......... 514/322; 546/199
See application file for complete search history.

(56) References Cited

U.S. PATENT DOCUMENTS

| 5,567,711 | A | 10/1996 | Sheppard et al. | |
|---|---|---|---|---|
| 6,727,246 | B2 * | 4/2004 | Bernotas et al. | 514/234.5 |
| 6,767,912 | B2 * | 7/2004 | Zhou et al. | 514/300 |

FOREIGN PATENT DOCUMENTS

| WO | WO97 49382 A | 12/1997 |
|---|---|---|
| WO | WO97 49698 A | 12/1997 |
| WO | WO97 49699 A | 12/1997 |
| WO | WO03 013510 A | 2/2003 |

OTHER PUBLICATIONS

Allen et al. "Preparation of heterocyclic . . . " CA 128:102084 (1998).*
Bernotas et al. "1-(ainoalkyl)-3-. . . " CA 140:27760 (2003).*
Zou et al. "Preparation of . . . " CA 137:78951 (2002).*
Cole et al. "conformationally constrained . . . " Bioorg. Med. Chem. Lett. v.15, p. 4780-4785 (2005).*

* cited by examiner

*Primary Examiner*—Celia Chang
(74) *Attorney, Agent, or Firm*—Gloria K. Szakiel; Scott K. Larsen; David R. Kurlandsky

(57) ABSTRACT

The present invention provides a compound of formula I and the use thereof for the treatment of a central nervous system disorder related to or affected by the 5-HT6 receptor.

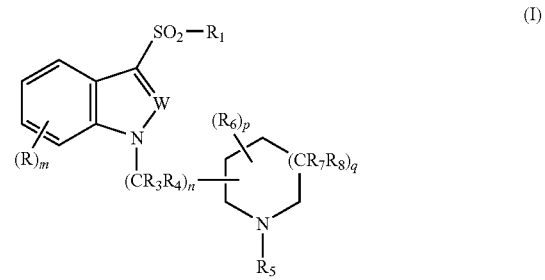

(I)

14 Claims, No Drawings

1-HETEROCYCLYLALKYL-3-SULFONYLINDOLE OR -INDAZOLE DERIVATIVES AS 5-HYDROXYTRYPTAMINE-6 LIGANDS

This is a divisional of copending application Ser. No. 10/621,698 filed on Jul. 17, 2003 which application claims the benefit of provisional application Ser. No. 60/396,958, filed Jul. 18, 2002, the entire disclosure of each application is hereby incorporated by reference.

BACKGROUND OF THE INVENTION

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; E I Mestikawy, S. *Brain Research*, 1997, 746, 207-219). The ability of known 5-HT6 receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537-1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology*, 2000, 130(1), 23-26). Animal studies of memory and learning with a known selective 5-HT6 antagonist found some positive effects (Rogers, D. C.; Hatcher, P. D.; Hagan, J. J. *Society of Neuroscience, Abstracts* 2000, 26, 680).

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Taken together, the above studies strongly suggest that compounds which are 5-HT6 receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a 1-heterocyclylalkyl-3-sulfonylindole or -indazole compound of formula I

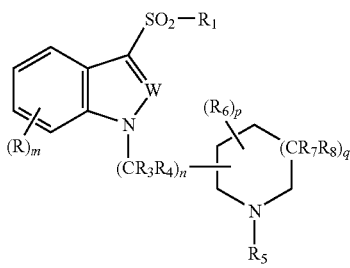

wherein

W is N or $CR_2$;

R is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;

$R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;

$R_2$ is H, halogen, or a $C_1$-$C_6$alkyl, $C_1$-$C_6$alkoxy, $C_3$-$C_7$cycloalkyl, aryl or heteroaryl group each optionally substituted;

$R_3$ and $R_4$ are each independently H or an optionally substituted $C_1$-$C_6$alkyl group;

$R_5$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;

$R_6$ is a $C_1$-$C_6$alkyl, $C_3$-$C_7$cycloalkyl, $C_2$-$C_6$alkenyl or $C_2$-$C_6$alkynyl group each optionally substituted;

$R_7$ and $R_8$ are each independently H or a $C_1$-$C_6$alkyl, $C_3$-$C_7$cycloalkyl, $C_2$-$C_6$alkenyl or $C_2$-$C_6$alkynyl group each optionally substituted;

m, n and p are each independently 0 or an integer of 1, 2 or 3;

q and x are each independently 0 or an integer of 1 or 2;

$R_9$, $R_{10}$, $R_{13}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{11}$ and $R_{12}$ are each independently H or an optionally $C_1$-$C_6$alkyl group or $R_{11}$ and $R_{12}$ may be taken together with the atom to which they are attached to form a 5- to 7-member ring optionally containing another heteroatom selected from O, N or S;

$R_{14}$ and $R_{15}$ are each independently H or an optionally substituted $C_1$-$C_4$alkyl group or $R_{14}$ and $R_{15}$ may be taken together with the atom to which they are attached to form a 5- to 7-membered ring optionally containing another heteroatom selected from O, $NR_{18}$ or $SO_x$;

$R_{16}$ is a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; and $R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; or the stereoisomers thereof or the pharmaceutically acceptable salts thereof.

The present invention also provides methods and compositions useful for the therapeutic treatment of a central nervous system disorder related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd.

Surprisingly, it has now been found that 1-heterocyclylalkyl-3-sulfonylindole and -indazole derivatives of formula I demonstrate 5-HT6 affinity. Advantageously, said indole and indazole derivatives may be used as effective therapeutic agents for the treatment of central nervous system (CNS) disorders associated with or affected by the 5-HT6 receptor. Accordingly, the present invention provides 1-heterocyclylalkyl-3-sulfonylindole and -indazole derivatives of formula I

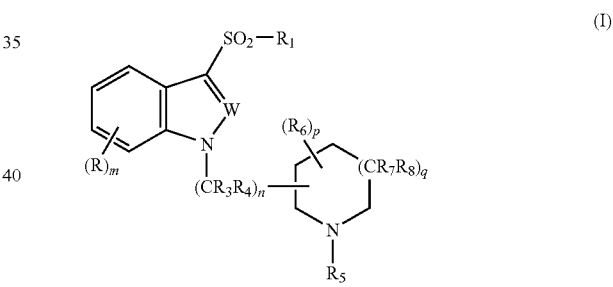

wherein

W is N or $CR_2$;

R is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;

$R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1, 2 or 3 additional heteroatoms selected from N, O or S;

$R_2$ is H, halogen, or a $C_1$-$C_6$alkyl, $C_1$-$C_6$alkoxy, $C_3$-$C_7$cycloalkyl, aryl or heteroaryl group each optionally substituted;

$R_3$ and $R_4$ are each independently H or an optionally substituted $C_1$-$C_6$alkyl group;

$R_5$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;

R₆ is a C₁-C₆alkyl, C₃-C₇cycloalkyl, C₂-C₆alkenyl or C₂-C₆alkynyl group each optionally substituted;

R₇ and R₈ are each independently H or a C₁-C₆alkyl, C₃-C₇cycloalkyl, C₂-C₆alkenyl or C₂-C₆alkynyl group each optionally substituted;

m, n and p are each independently 0 or an integer of 1, 2 or 3;

q and x are each independently 0 or an integer of 1 or 2;

R₉, R₁₀, R₁₃ and R₁₇ are each independently H or a C₁-C₆alkyl, C₂-C₆alkenyl, C₂-C₆alkynyl, C₃-C₆cycloalkyl, cycloheteroalkyl, aryl or heteroaryl group each optionally substituted;

R₁₁ and R₁₂ are each independently H or an optionally C₁-C₆alkyl group or R₁₁ and R₁₂ may be taken together with the atom to which they are attached to form a 5- to 7-member ring optionally containing another heteroatom selected from O, N or S;

R₁₄ and R₁₅ are each independently H or an optionally substituted C₁-C₄alkyl group or R₁₄ and R₁₅ may be taken together with the atom to which they are attached to form a 5- to 7-membered ring optionally containing another heteroatom selected from O, NR₁₈ or SOₓ;

R₁₆ is a C₁-C₆alkyl, C₂-C₆alkenyl, C₂-C₆alkynyl, C₃-C₇cycloalkyl, cycloheteroalkyl, aryl or heteroaryl group each optionally substituted;

x is 0 or an integer of 1 or 2; and

R₁₈ is H or a C₁-C₆alkyl, C₂-C₆alkenyl, C₂-C₆alkynyl, C₃-C₇cycloalkyl, cycloheteroalkyl, aryl or heteroaryl group each optionally substituted; or the stereoisomers thereof or the pharmaceutically acceptable salts thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X is NR', O or S; and R' is H or an optional substituent as described hereinbelow:

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W₂ is NR', O or S; and R' is H or an optional substituent as described hereinbelow:

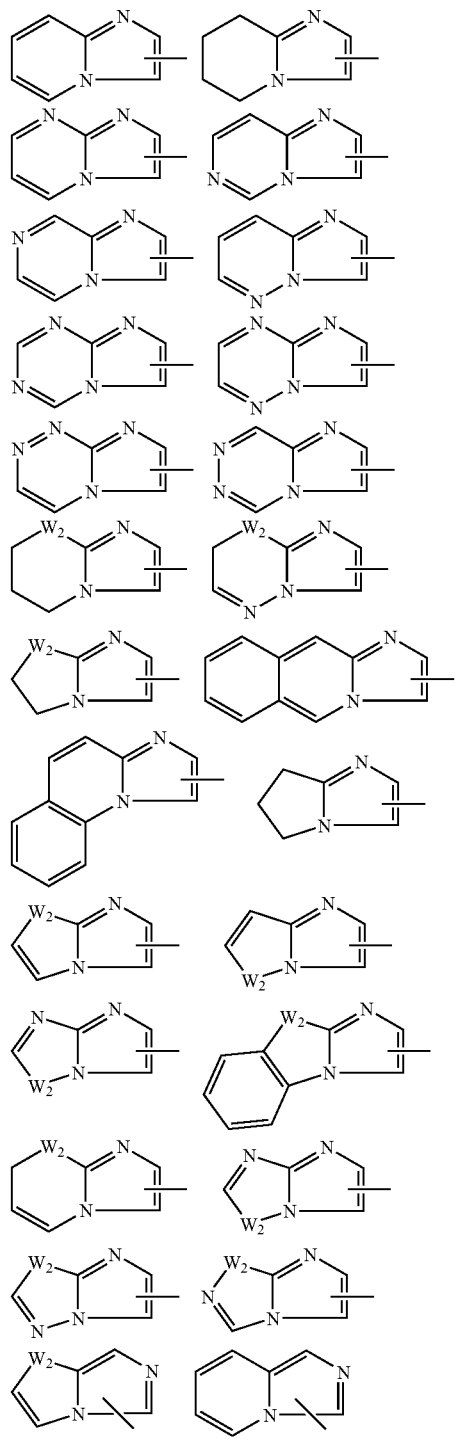

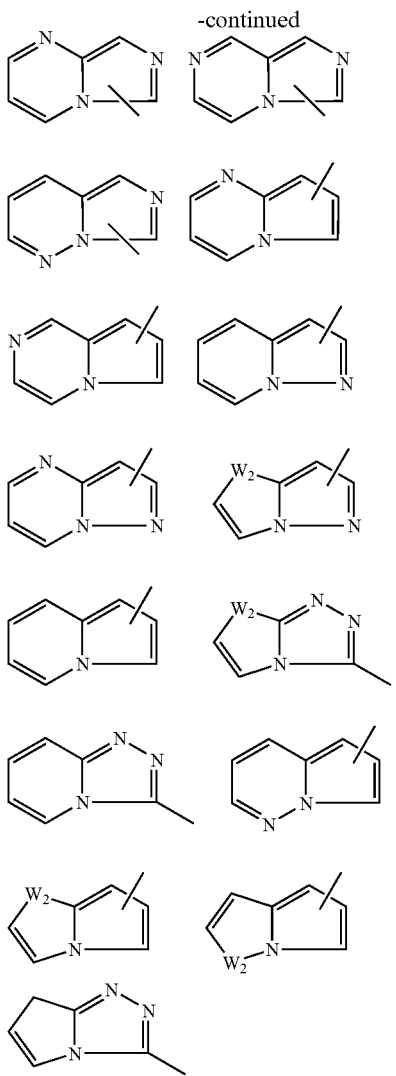

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl as designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein n is 0. Also preferred are those compounds of formula I wherein $R_5$ is H. Another group of preferred compounds of formula I are those compounds wherein $R_1$ is an optionally substituted phenyl group.

More preferred compounds of the invention are those formula I compounds wherein n is 0 and q is 0 or 1. Another group of more preferred compounds are those formula I compounds wherein n, m and p are each 0. Further more preferred formula I compounds are those compounds wherein n is 0; q is 0 or 1; and the piperidinyl or pyrrolidinyl group is attached in the 3-position.

Examples of preferred compounds of formula I include:
6-chloro-3-(phenylsulfonyl)-1-(piperidin-4-ylmethyl)-1H-indole
6-fluoro-3-(phenylsulfonyl)-1-(piperidin-4-ylmethyl)-1H-indole;
5-chloro-3-(phenylsulfonyl)-1-(piperidin-4-ylmethyl)-1H-indole;
6-fluoro-3-(phenylsulfonyl)-1-(piperidin-4-ylmethyl)-1H-indole;
6-methoxy-3-(phenylsulfonyl)-1-(piperidin-4-ylmethyl)-1H-indole;
6-methyl-3-(phenylsulfonyl)-1-(piperidin-4-ylmethyl)-1H-indole;
3-(4-methylphenylsulfonyl)-1-(piperidin-4-ylmethyl)-1H-indole;
6-bromo-3-(phenylsulfonyl)-1-(piperidin-4-ylmethyl)-1H-indole;
4-chloro-3-(phenylsulfonyl)-1-(piperidin-4-ylmethyl)-1H-indole;
7-methoxy-3-(phenylsulfonyl)-1-(piperidin-4-ylmethyl)-1H-indole;
6-hydroxy-3-(phenylsulfonyl)-1-(piperidin-4-ylmethyl)-1H-indole;
6-chloro-3-(4-fluorophenylsulfonyl)-1-(piperidin-4-ylmethyl)-1H-indole;
6-fluoro-3-(3-fluorophenylsulfonyl)-1-(piperidin-4-ylmethyl)-1H-indole;

5-chloro-3-(3-chlorophenylsulfonyl)-1-(piperidin-4-ylmethyl)-1H-indole;
3-(2-chlorophenylsulfonyl)-6-fluoro-1-(piperidin-4-ylmethyl)-1H-indole;
3-(2-fluorophenylsulfonyl)-6-methoxy-1-(piperidin-4-ylmethyl)-1H-indole;
3-(4-methylphenylsulfonyl)-1-(piperidin-3-ylmethyl)-1H-indole;
6-bromo-3-(phenylsulfonyl)-1-(piperidin-3-ylmethyl)-1H-indole;
4-chloro-3-(phenylsulfonyl)-1-(piperidin-3-ylmethyl)-1H-indole;
7-methoxy-3-(phenylsulfonyl)-1-(piperidin-3-ylmethyl)-1H-indole;
6-hydroxy-3-(phenylsulfonyl)-1-(piperidin-3-ylmethyl)-1H-indole;
6-chloro-3-(4-fluorophenylsulfonyl)-1-(piperidin-2-ylmethyl)-1H-indole;
6-fluoro-3-(3-fluorophenylsulfonyl)-1-(piperidin-2-ylmethyl)-1H-indole;
5-chloro-3-(3-chlorophenylsulfonyl)-1-(piperidin-2-ylmethyl)-1H-indole;
3-(2-chlorophenylsulfonyl)-6-fluoro-1-(piperidin-2-ylmethyl)-1H-indole;
3-(2-fluorophenylsulfonyl)-6-methoxy-1-(piperidin-2-ylmethyl)-1H-indole;
3-(phenylsulfonyl)-1-(piperidin-4-ylmethyl)-1H-indole;
3-(phenylsulfonyl)-1-(piperidin-3-ylmethyl)-1H-indole;
3-(phenylsulfonyl)-1-(piperidin-2-ylmethyl)-1H-indole;
3-(phenylsulfonyl)-1-(pyrrolidin-3-ylmethyl)-1H-indole;
3-(phenylsulfonyl)-1-(pyrrolidin-2-ylmethyl)-1H-indole;
6-methyl-3-(phenylsulfonyl)-1-(pyrrolidin-3-ylmethyl)-1H-indole;
3-(4-methylphenylsulfonyl)-1-(pyrrolidin-3-ylmethyl)-1H-indole;
6-bromo-3-(phenylsulfonyl)-1-(pyrrolidin-3-ylmethyl)-1H-indole;
4-chloro-2-methyl-3-(phenylsulfonyl)-1-(pyrrolidin-2-ylmethyl)-1H-indole;
7-methoxy-3-(phenylsulfonyl)-1-(pyrrolidin-2-ylmethyl)-1H-indole;
6-hydroxy-3-(phenylsulfonyl)-1-(pyrrolidin-2-ylmethyl)-1H-indole;
1-(piperidin-2-ylmethyl)-3-(2-pyridinylsulfonyl)-1H-indole;
1-(piperidin-3-ylmethyl)-3-(2-pyridinylsulfonyl)-1H-indole;
3-(2-pyridinylsulfonyl)-1-(pyrrolidin-3-ylmethyl)-1H-indole;
3-(2-pyridinylsulfonyl)-1-(pyrrolidin-2-ylmethyl)-1H-indole;
1-(piperidin-4-ylmethyl)-3-(2-thienylsulfonyl)-1H-indole;
1-(piperidin-3-ylmethyl)-3-(2-thienylsulfonyl)-1H-indole;
1-(piperidin-2-ylmethyl)-3-(2-thienylsulfonyl)-1H-indole;
1-(pyrrolidin-3-ylmethyl)-3-(3-thienylsulfonyl)-1H-indole;
2-(pyrrolidin-2-ylmethyl)-3-(3-thienylsulfonyl)-1H-indole;
3-phenylsulfonyl)-1-piperidin-4-yl-1H-indole;
3-phenylsulfonyl)-1-piperidin-3-yl-1H-indole;
3-phenylsulfonyl)-1-pyrrolidin-3-yl-1H-indole;
1-(1-benzylpiperidin-4-yl)-3-(phenylsulfonyl)-1H-indole;
1-(1-benzylpiperidin-3-yl)-3-(phenylsulfonyl)-1H-indole;
1-(1-benzylpyrrolidin-3-yl)-3-(phenylsulfonyl)-1H-indole;
3-(3-chlorophenylsulfonyl)-1-piperidin-4-yl-1H-indole;
3-(4-fluorophenylsulfonyl)-1-piperidin-3-yl-1H-indole;
3-(2-fluorophenylsulfonyl)-1-pyrrolidin-3-yl-1H-indole;
1-(1-methylpiperidin-4-yl)-3-(phenylsulfonyl)-1H-indole;
1-(1-ethylpiperidin-3-yl)-3-(phenylsulfonyl)-1H-indole;
1-(1-phenethylpyrrolidin-3-yl)-3-(phenylsulfonyl)-1H-indole;
1-piperidin-4-yl-3-(2-pyridylsulfonyl)-1H-indole;
1-piperidin-3-yl-3-(2-thienylsulfonyl)-1H-indole;
1-pyrrolidin-3-yl-3-(3-thienylsulfonyl)-1H-indole;
3-(phenylsulfonyl)-1-[(2R)-pyrrolidin-2-ylmethyl]-1H-indazole;
3-(phenylsulfonyl)-1-[(2S)-pyrrolidin-2-ylmethyl]-1H-indazole;
6-chloro-3-(phenylsulfonyl)-1-(piperidin-4-ylmethyl)-1H-indazole;
6-fluoro-3-(phenylsulfonyl)-1-(piperidin-4-ylmethyl)-1H-indazole;
5-chloro-3-(phenylsulfonyl)-1-(piperidin-4-ylmethyl)-1H-indazole;
6-fluoro-3-(phenylsulfonyl)-1-(piperidin-4-ylmethyl)-1H-indazole;
6-methoxy-3-(phenylsulfonyl)-1-(piperidin-4-ylmethyl)-1H-indazole;
6-methyl-3-(phenylsulfonyl)-1-(piperidin-4-ylmethyl)-1H-indazole;
3-(4-methylphenylsulfonyl)-1-(piperidin-3-ylmethyl)-1H-indazole;
6-bromo-3-(phenylsulfonyl)-1-(piperidin-3-ylmethyl)-1H-inazdole;
6-methyl-3-(phenylsulfonyl)-1-(pyrrolidin-3-ylmethyl)-1H-indazole;
3-(4-methylphenylsulfonyl)-1-(pyrrolidin-3-ylmethyl)-1H-indazole;
3-(2-pyridinylsulfonyl)-1-(pyrrolidin-2-ylmethyl)-1H-indazole;
1-(piperidin-4-ylmethyl)-3-(2-thienylsulfonyl)-1H-indazole;
1-(pyrrolidin-3-ylmethyl)-3-(3-thienylsulfonyl)-1H-indazole;
1-(pyrrolidin-2-ylmethyl)-3-(3-thienylsulfonyl)-1H-indazole;
3-(phenylsulfonyl)-1-(piperidin-4-yl)-1H-indazole;
3-(phenylsulfonyl)-1-(pyrrolidin-3-yl)-1H-indazole;
1-(1-benzylpiperidin-4-yl)-3-(phenylsulfonyl)-1H-indazole;
1-(1-benzylpiperidin-3-yl)-3-(phenylsulfonyl)-1H-indazole;
1-(1-benzylpyrrolidin-3-yl)-3-(phenylsulfonyl)-1H-indazole;
3-(3-chlorophenylsulfonyl)-1-(piperidin-4-yl)-1H-indazole;
3-(4-fluorophenylsulfonyl)-1-(piperidin-3-yl)-1H-indazole;

the stereoisomers thereof; or the pharmaceutically acceptable salts thereof.

Compounds of formula I may be prepared using conventional synthetic methods and, if required, standard separation or isolation techniques.

For example, compounds of formula I wherein n is 0; W is $CR_2$; and $R_5$ is H (Ia) may be prepared by the reductive amination of the compound of formula II with a protected azinone of formula III to give the intermediate of formula IV; reacting the formula IV intermediate with an amide ketal of formula VII in the presence of an acid such as p-toluenesulfonic acid to give the enamine of formula V; cyclizing said enamine in the presence of an acid such as aqueous HCL to give the compound of VI; and deprotecting said formula VI compound to give the desired product of Ia. Those compounds of formula I wherein n is 0; W is $CR_2$ and $R_5$ is other than H (Ib) may be readily prepared by alkylating the formula Ia compound with an alkylating agent of formula VII. The reactions are shown in flow diagram I wherein P represents a protecting group and L' represents a leaving group.

Flow Diagram I

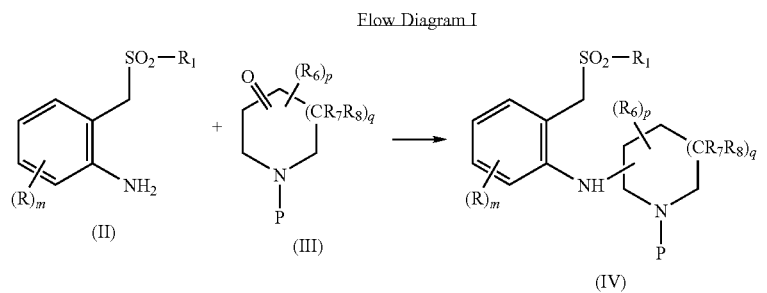

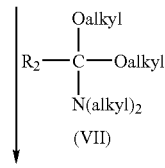

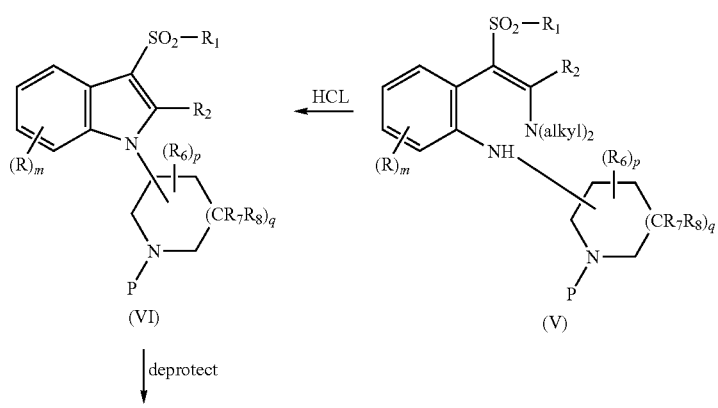

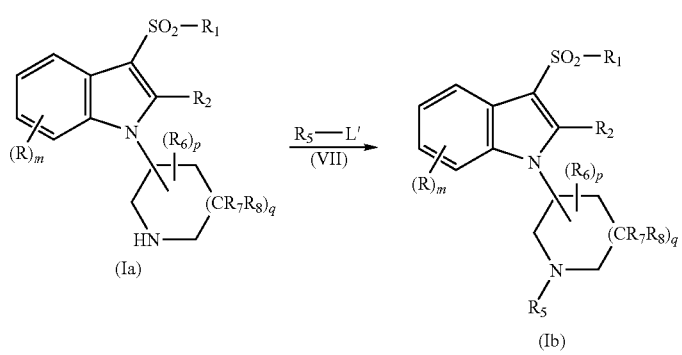

Compounds of formula I wherein $R_5$ is H (Ia) may also be prepared by reacting a compound of formula VIII with a protected azacyclic compound of formula IX in the presence of a base to give the protected compound of formula X; deprotection gives the desired compound of Ia. Alkylation of Ia as shown in flow diagram I hereinabove gives the compound of formula I wherein $R_5$ is other than H (Ib). The reaction is shown in flow diagram II wherein P represents a protecting group and L and L' represent a leaving group.

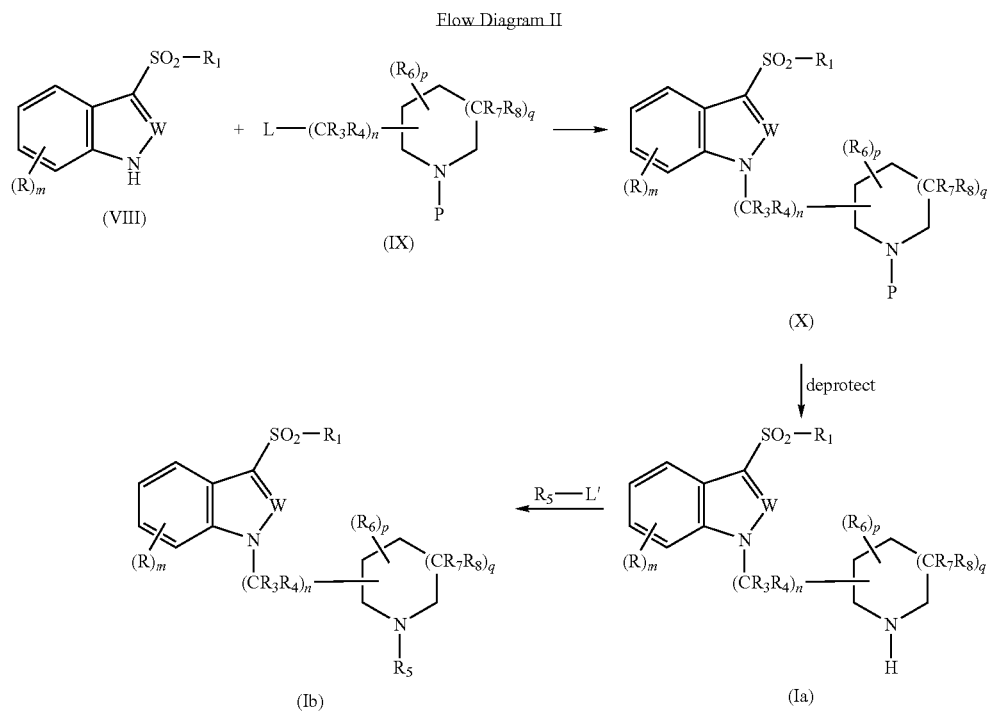

Flow Diagram II

Protecting groups suitable for use in the reactions shown hereinabove include t-butylcarboxylate, benzyl, acetyl, benzyloxycarbonyl, or any conventional group known to protect a basic nitrogen in standard synthetic procedures.

Conditions suitable for deprotecting compounds of formula VI or X may vary depending upon the nature of the protecting group. For example, for a t-butyl-carboxylate protecting group, deprotection may take place in the presence of an acid such as trifluoroacetic acid or HCl and optionally an aprotic solvent such as dioxane; for a benzyl protecting group, deprotection may take place via catalytic hydrogenation.

Leaving groups suitable for use in the reactions shown hereinabove include Cl, Br, I, OH, tosyl, mesyl or the like.

Compounds of formula VIII may be prepared using conventional synthetic methods and, if required, standard separation and isolation techniques. For example, for compounds of formula VIII wherein W is $CR_2$ (VIIIa), a nitrobenzene compound of formula XI may be reacted with a chloromethylsulfonyl compound of formula XII in the presence of a strong base to give the intermediate of formula XIII; said formula XIII intermediate may then be treated with a reducing agent such as Fe, Zn or Sn in the presence of an acid to give the amine of formula II; said amine may then be reacted with the appropriate orthoester of formula XV to give the formula XVI compound; and said formula XVI compound may be cyclized in the presence of a base to give the desired formula VIIIa 3-sulfonylindole. The general synthetic method is described by W. Wojciechowski and M. Makosza, *Synthesis* 1986, 651-653. Similarly, the formula II amine may be reacted with $NaNO_2$ in the presence of an acid to give those compounds of formula VIII wherein W is N (VIIIb). The reaction sequences are shown in flow diagram III.

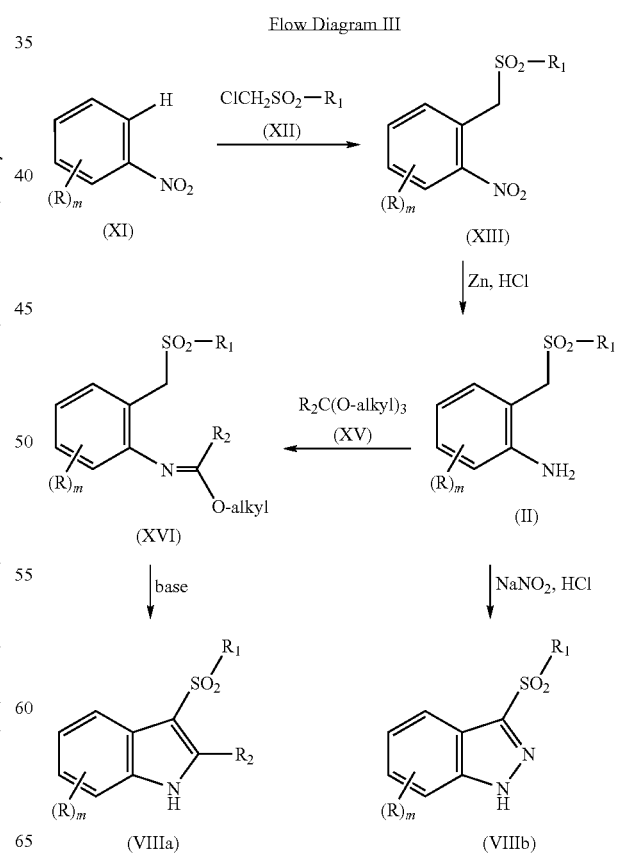

Flow Diagram III

Compounds of formula VIII may also be prepared directly from an indole or indazole of formula XVII by reacting the formula XVII substrate with iodine to give the 3-iodoindole or -indazole of formula XVIII; coupling the formula XVIII compound with an appropriate thiol of formula XIX to give the 3-thioindole or -indazole of formula XX and oxidizing said formula XX compound with a conventional oxidizing agent such as $H_2O_2$, m-chloroperbenzoic acid, or the like to afford the desired formula VIII intermediate. The reaction is shown in flow diagram IV.

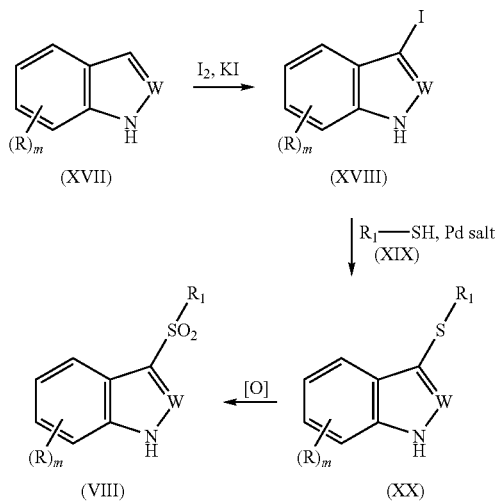

Flow Diagram IV

Alternatively, the formula XX 3-thioindole or -azaindole compound may be prepared in a single step from the formula XVII substrate by reacting the formula XVII compound with the formula XIX thiol in the presence of iodine, preferably in a polar solvent such as aqueous alcohol. The thus-obtained formula XX compound may then be oxidized as shown hereinabove to give the formula VIII intermediate. The thus-obtained formula VIII intermediate may then be carried on to the desired compounds of formula I via the alkylation of the basic indole or indazole nitrogen atom as shown in flow diagram II hereinabove.

Advantageously, the present invention provides a process for the preparation of a compound of formula I which comprises reacting a compound of formula VIII with a protected azacyclic compound of formula IX in the presence of a first base to give the protected amine of formula X; and deprotecting said amine to give the compound of formula I wherein $R_5$ is H optionally alkylating said compound with an alkylating agent, $R_5$-L', wherein L' is a leaving group in the presence of a second base to give the compound of formula I wherein $R_5$ is other than H. The process of the invention is illustrated in flow diagram II hereinabove.

Protecting groups suitable for use in the process of the invention include t-butylcarboxylate, benzyl, acetyl, benzyloxycarbonyl, or any conventional group known to protect a basic nitrogen.

Leaving groups suitable for use in the process of the invention include Cl, Br, I, OH, tosyl, mesyl or the like.

Bases suitable for use as the first base in the process of the invention include strong bases such as NaH, KOt-Bu, NaOH, or any conventional base capable of removing a proton from an indole or indazole nitrogen atom.

Bases suitable for use as the second base in the inventive process include weak bases such as $K_2CO_3$, $Na_2CO_3$, tertiary organic amines such as triethylamine or the like.

Advantageously, the formula I compounds of the invention are useful for the treatment of CNS disorders relating to or affected by 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated with withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention.

Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

The term HNMR designates proton nuclear magnetic resonance. The terms $CH_2Cl_2$, THF and DMF designate methylene chloride, tetrahydrofuran and dimethyl formamide, respectively. All chromatography is performed using $SiO_2$ as support.

EXAMPLE 1

Preparation of 3-(Phenylthio)-1H-indole

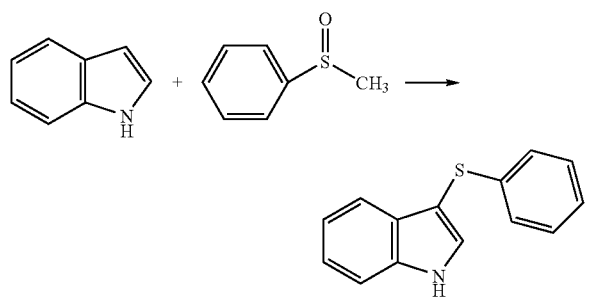

A solution of methyl phenyl sulfoxide (4.0 g, 147 mmol) in $CH_2Cl_2$ is cooled to −78° C., treated dropwise with trifluoroacetic anhydride (4.0 mL, 5.99 g, 28.5 mmol), stirred for 30 min at −78° C., treated with a solution of indole (1.82 g, 15.6 mmol) in $CH_2Cl_2$, stirred for 30 min at −78° C., treated with triethylamine (20 mL, 145 mmol), stirred for 4 days at ambient temperatures and diluted with water. The phases are separated. The organic phase is dried over $MgSO_4$ and concentrated in vacuo. The resultant residue is chromatographed (1:99 methanol:$CH_2Cl_2$) to give the title product as a white solid, 3.08 g (88% yield), mp 149-151° C., characterized by mass spectral and HNMR analyses.

EXAMPLE 2

Preparation of 3-(Phenylsulfonyl)-1H-indole

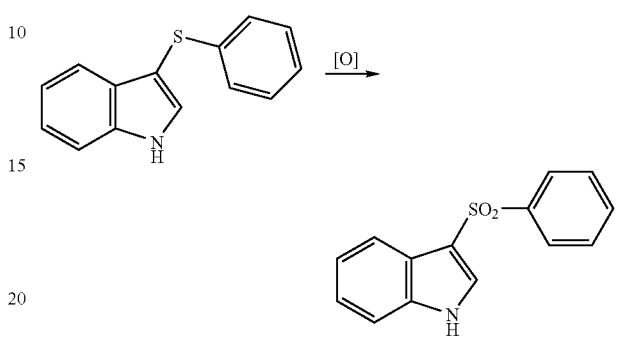

A stirred solution of 3-(phenylthio)-1H-indole (12.0 g, 53.3 mmol) in $CH_2Cl_2$ (800 mL) is chilled to 0° C., treated with 3-chloroperbenzoic acid (20.2 g, 117 mmol) and stirred for 4 h at ambient temperature. The reaction is washed sequentially with water and saturated $NaHCO_3$, dried over $MgSO_4$ and concentrated in vacuo. Chromatography (1:49 methanol:$CH_2Cl_2$) of the resultant residue affords the title compound as a white solid, 9.83 g (72% yield), mp 149-151° C., characterized by mass spectral and HNMR analyses.

EXAMPLE 3

Preparation of t-Butyl 4-[3-(Phenvisulfonyl)-1H-indol-1-ylmethyl]piperidine-1-carboxylate

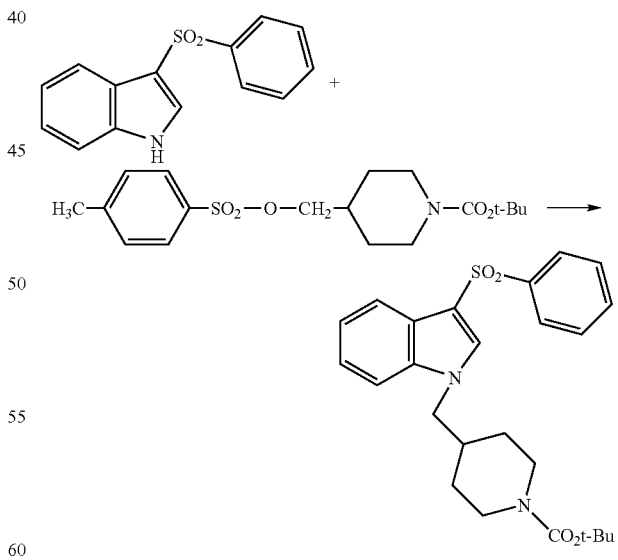

A stirred solution of 3-(phenylsulfonyl)-1H-indole (700 mg, 2.72 mmol) in anhydrous DMF is chilled to 0° C., treated with 60% sodium hydride in mineral oil (163 mg, 4.08 mmol) stirred for 2 h at ambient temperature, treated with 4-(toluene-4-sulfonyloxymethyl)-piperidine-1-carboxylic acid tert-butyl ester[1] (1.26 g, 3.40 mmol), stirred for 16 h at 55° C., cooled to ambient temperature, diluted with water and extracted with $CH_2Cl_2$. The combined organic extracts are concentrated in vacuo. The resultant residue is triturated under hexanes and crystallized from methanol/water to afford the title product as a light-yellow solid, 0.97 g, mp 181-182° C., identified by HNMR and mass spectral analyses.

[1] Journal of Labeled Compound Radiopharm, 1999, 42, 1289-1300.

EXAMPLE 4

Preparation of 3-(Phenylsulfonyl)-1-(Piperidin-4-ylmethyl)-1H-indole Hydrochloride

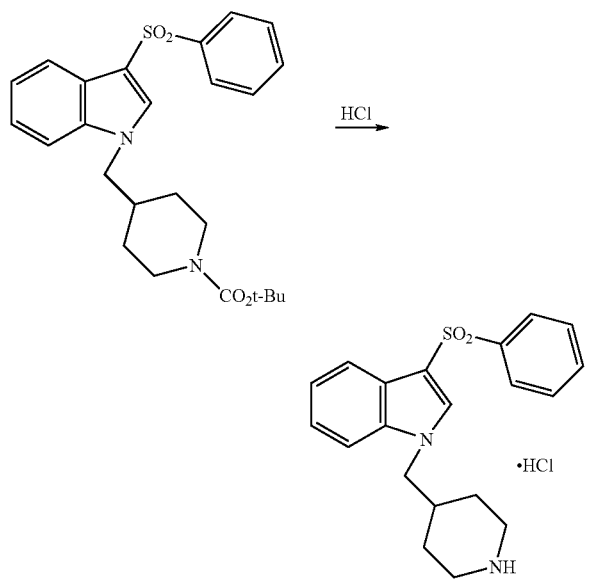

A stirred solution of 4-[3-(phenylsulfonyl)-1H-indol-ylmethyl]-piperidine-1-carboxylic acid tert-butyl ester (500 mg, 1.10 mmol) in dioxane is treated with 4N HCl in dioxane (4.5 mL, 18 mmol), stirred for 5 h at ambient temperature and concentrated in vacuo. Crystallization of the resultant solid residue from ethanol:ether affords the title compound as a white solid, 351 mg (82% yield), mp>250° C., identified by HNMR and mass spectral analyses.

EXAMPLE 5

Preparation of 2-(Phenylsulfonylmethyl)-1-nitrobenzene

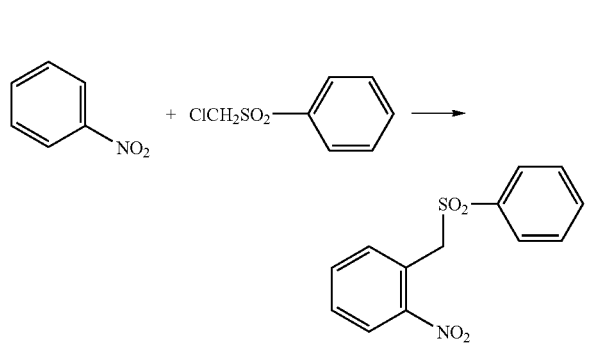

A solution of nitrobenzene (3.08 g, 25.0 mmol) and chloromethylphenylsulfone (4.76 g, 25.0 mmol) in dry THF is cooled to −50° C. and treated with 1.0M KO$^t$Bu/THF (55.0 mL, 55.0 mmol). The reaction is allowed to warm to −30° C. over 1 h, treated with glacial acetic acid (3.6 mL), warmed to 20° C., treated with water and extracted with $CH_2Cl_2$. The combined extracts are dried over $MgSO_4$ and concentrated in vacuo. Chromatography (1:1 ethyl acetate:hexanes) of the resultant residue give the title product as a white solid, 5.62 g, (81% yield), mp 106-108° C., identified by mass spectral and HNMR analyses.

EXAMPLE 6

Preparation of 2-(Phenylsulfonylmethyl)aniline

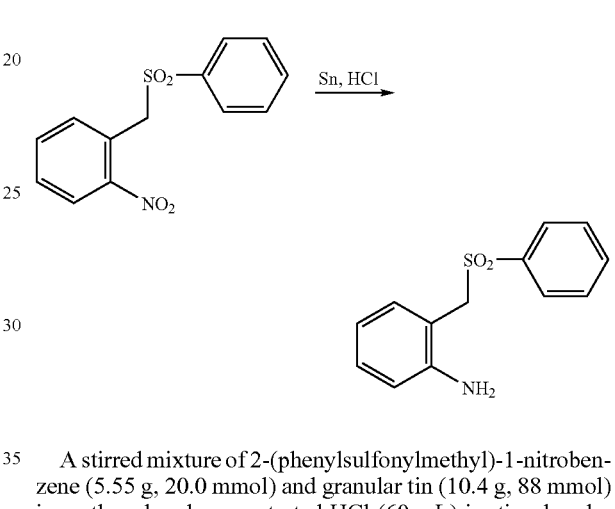

A stirred mixture of 2-(phenylsulfonylmethyl)-1-nitrobenzene (5.55 g, 20.0 mmol) and granular tin (10.4 g, 88 mmol) in methanol and concentrated HCl (60 mL) is stirred under nitrogen at 45° C. for 5 h, cooled to ambient temperature over an 18 h period, poured onto $NaHCO_3$ (80 g) with stirring, treated with water and extracted with ethyl acetate. The combined extracts are washed with brine (2×100 mL), dried over $MgSO_4$, and concentrated in vacuo to afford the title product as an off-white solid, 4.41 g (89%) mp 175-176° C., identified by HNMR and mass spectral analyses.

EXAMPLE 7

Preparation of 1-Benzyl-3-{[2-(phenylsulfonyl)methyl]aniline}piperidine

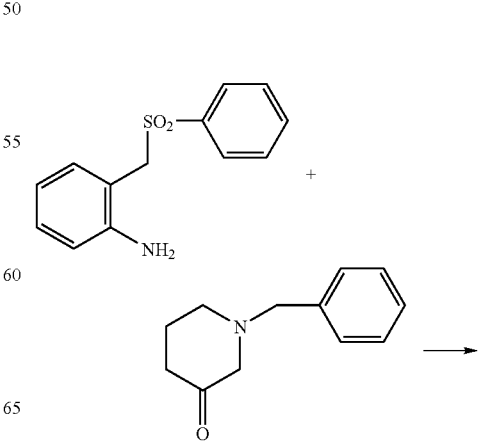

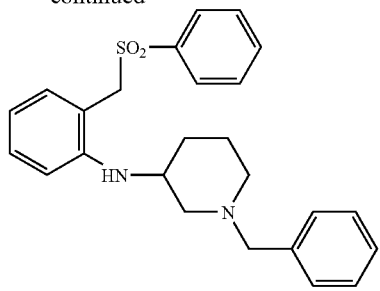

A mixture of 2-[(phenylsulfonyl)methyl]aniline (1.24 g, 5.00 mmol), Na$_2$SO$_4$ (7.1 g, 50 mmol), and 1-benzyl-3-piperidinone (2.26 g, 10.0 mmol) in glacial acetic acid is stirred under nitrogen at ambient temperature for 45 min, treated with NaBH(OC(O)CH$_3$)$_3$ (3.16 g, 15.0 mmol), stirred for 2.5 h, poured slowly onto a stirred mixture of NaHCO$_3$ and water and extracted with ethyl acetate. The combined extracts are washed with brine, dried over MgSO$_4$, and concentrated in vacuo. The resultant residue is chromatographed (1:1 ethyl acetate:hexanes) to afford the title product as a viscous, pale yellow oil, 1.94 g (92% yield), identified by HNMR and mass spectral analyses.

EXAMPLE 8

Preparation of 1-(1-Benzylpiperidin-3-yl)-3-(phenylsulfonyl)-1H-indole

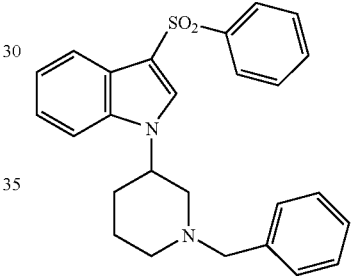

A solution of 1-benzyl-3-{[2-(phenylsulfonyl)methyl]aniline}-piperidine (1.85 g, 4.40 mmol) and para-toluenesulfonic acid (ptsa) monohydrate (0.20 g) in N,N-dimethylformamide dimethyl acetal is heated at reflux temperature for 76 h, and concentrated in vacuo. The resultant residue is treated with saturated aqueous NaHCO$_3$ and extracted with CH$_2$Cl$_2$. The combined extracts are concentrated in vacuo to an orange oil. This oil is rechromatographed (100% ethyl acetate) to give an orange oil. The oil is stirred in ethanol and 2.0M aqueous HCl at ambient temperature for 2.5 h, treated with saturated aqueous NaHCO$_3$ and extracted with CH$_2$Cl$_2$. The extracts are combined, dried over MgSO$_4$ and concentrated in vacuo. The resultant residue is chromatographed (1:1 ethyl acetate:hexanes) to afford the title product as a light orange solid, 0.56 g (30% yield), mp 219-221° C., identified by HNMR and mass spectral analyses.

EXAMPLE 9

Preparation of 3-(Phenylsulfonyl)-1-(piperidin-3-yl)-1H-indole Hydrochloride

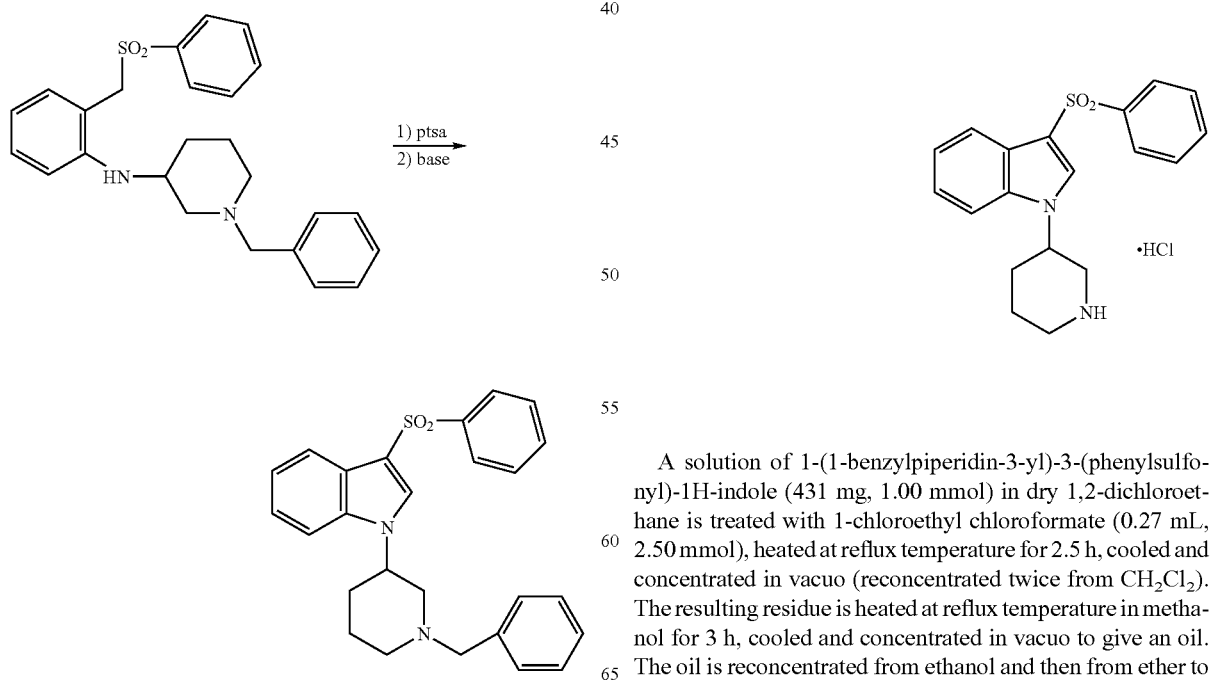

A solution of 1-(1-benzylpiperidin-3-yl)-3-(phenylsulfonyl)-1H-indole (431 mg, 1.00 mmol) in dry 1,2-dichloroethane is treated with 1-chloroethyl chloroformate (0.27 mL, 2.50 mmol), heated at reflux temperature for 2.5 h, cooled and concentrated in vacuo (reconcentrated twice from CH$_2$Cl$_2$). The resulting residue is heated at reflux temperature in methanol for 3 h, cooled and concentrated in vacuo to give an oil. The oil is reconcentrated from ethanol and then from ether to give a tan solid. The solid is triturated with ethanol and filtered. The filtercake is dried under vacuum to afford the title product as an off-white solid, 322 mg (85% yield), mp 254-256° C., identified by HNMR and mass spectral analyses.

EXAMPLES 10-13

Preparation of 1-Heterocyclyl-3-(Phenylsulfonyl)-1H-indole Derivatives

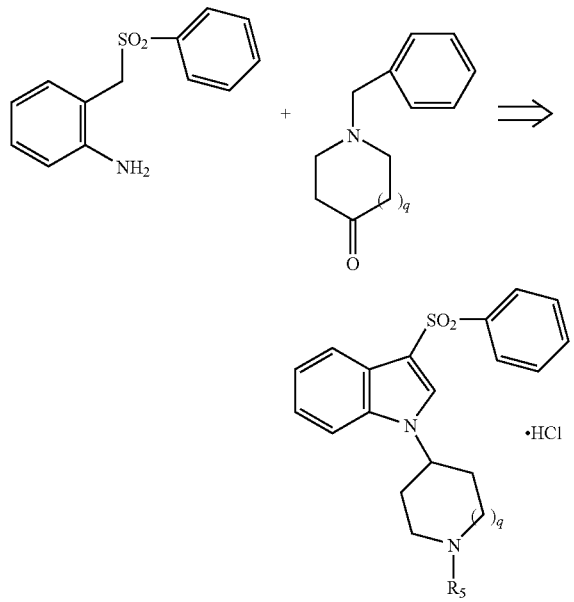

Using essentially the same procedures described in Examples 7 and 8 hereinabove and employing the appropriate protected piperidinone or pyrrolidinone reagent, the compounds shown in Table I are obtained and identified by HNMR and mass spectral analyses.

TABLE I

| Ex. No. | q | R5 | mp ° C. |
|---|---|---|---|
| 10 | 0 | benzyl | 140 (foam) |
| 11 | 0 | H | 209-211 |
| 12 | 1 | benzyl | 288-291 |
| 13 | 1 | H | 294-297 |

EXAMPLES 14-26

Preparation of 1-(3-Piperidinyl)-3-arylsulfonyl-1H-indole Derivatives

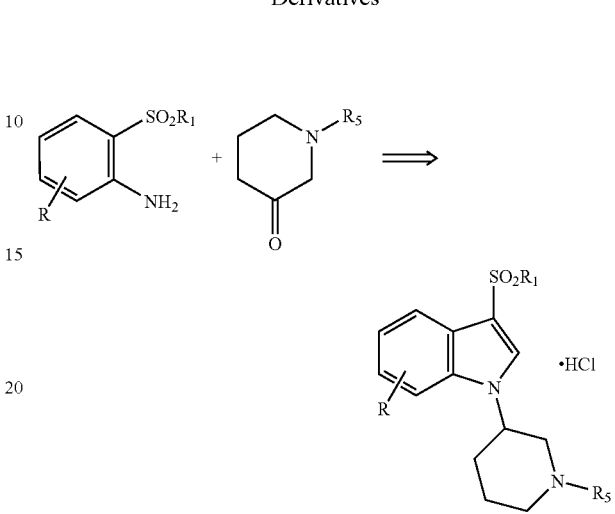

Using essentially the same procedures described in Examples 5 through 9 hereinabove and employing the appropriately substituted nitrobenzene, arylsulfonyl chloride and protected 3-piperidinone, the compounds shown in Table II are obtained and identified by HNMR and mass spectral analyses.

TABLE II

| Ex No | R | R1 | R5 | mp ° C. |
|---|---|---|---|---|
| 14 | H | 1-naphthyl | H | >180 (dec) |
| 15 | H | 8-quinolinyl | H | >195 (dec) |
| 16 | H | 3-F—$C_6H_4$ | H | >150 (dec) |
| 17 | H | 3-Cl—$C_6H_4$ | H | >150 (dec) |
| 18 | 5-$OCH_3$ | 3-F—$C_6H_4$ | H | 267-270 |
| 19 | 5-$OCH_3$ | 3-F—$C_6H_4$ | $CH_3$ | 262-265 |
| 20 | 5-F | 3-F—$C_6H_4$ | H | 275-278 |
| 21 | 5-F | 3-F—$C_6H_4$ | $CH_3$ | 255-257 |
| 22 | 5-Cl | 3-F—$C_6H_4$ | H | — |
| 23 | 5-Cl | 3-F—$C_6H_4$ | $CH_3$ | 242-245 |
| 24 | 5-$OCH_3$ | 3-F—$C_6H_4$ | $C_2H_5$ | 227-228 |
| 25 | 5-Cl | 3-F—$C_6H_4$ | $C_2H_5$ | 225-226 |
| 26 | H | 8-quinolinyl | $CH_3$ | >250 (dec) |

EXAMPLE 27

Preparation of 3-(Phenylsulfonyl)-1H-indazole

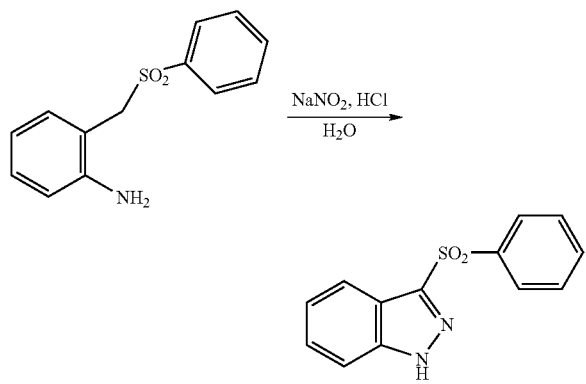

A stirred solution of 2-[(phenylsulfonyl)methyl]aniline (247 mg, 1.00 mmol) in 4N HCl (50 ml) is treated with a solution of $NaNO_2$ (100 mg, 1.5 mmol) in water at ice-bath temperatures, stirred for 30 min., neutralized with 10% NaOH and filtered. The filtercake is dissolved in $CH_2Cl_2$, dried over $MgSO_4$ and concentrated in vacuo to afford the title product as a tan solid, 240 mg (93% yield), mp 118° C., identified by mass spectral and HNMR analyses.

EXAMPLE 28

Preparation of 3-Phenylsulfonyl-1-(pyrrolidin-2-ylmethyl)-1H-indazole hydrochloride

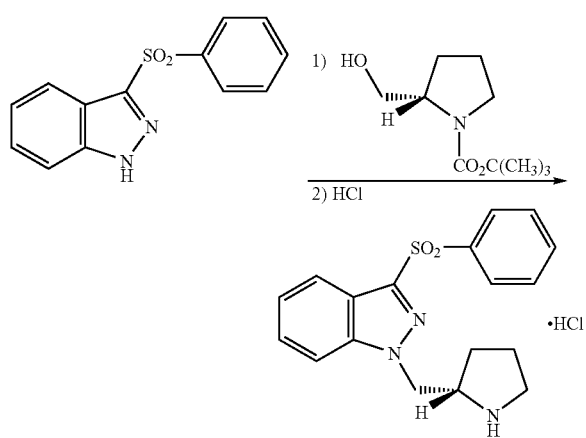

A mixture of 3-phenylsulfonyl-1H-indazole (258 mg, 1.00 mmol), N-t-BOC-D-prolinol (402 mg, 2.00 mmol) and triphenylphosphine (524 mg, 2.00 mmol) in THF is treated with diisopropyl azodicarboxylate (404 mg, 2.00 mmol) at room temperature, stirred overnight and concentrated in vacuo. The resultant residue is chromatographed (30/70 ethyl acetate/hexanes) to give the Boc-protected product contaminated with diisopropyl azodicarboxylate-derived by-product. This product mixture is treated with 4.0M HCl in dioxane (0.05 mL) in 5 mL methanol, stirred and concentrated in vacuo. This residue is dispersed in ether and filtered. The white solid filtercake is partitioned between ethyl acetate and saturated aqueous $NaHCO_3$. The organic phase is washed with water, dried over $MgSO_4$ and concentrated in vacuo. The resultant residue is chromatographed (90/10 ethyl acetate/2% ethanolic ammonia) to give the free amine of the title product. The amine is dissolved in methanol and treated with 4.0M HCl in dioxane and concentrated in vacuo to afford the title compound as a white solid, 65 mg (19% yield), mp 225-227° C., identified by HNMR and mass spectral analyses.

EXAMPLE 29

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6. The data are shown in Table III, below.

TABLE III

| Test Compound (Ex. No.) | 5-HT6 Binding Ki (nM) |
|---|---|
| 4 | 27 |
| 8 | 122 |
| 9 | 13 |
| 10 | 113 |
| 11 | 5 |
| 12 | 49 |
| 13 | 91 |
| 14 | 21 |
| 15 | 6 |
| 17 | 5 |
| 18 | 11 |
| 19 | 68 |
| 20 | 4 |
| 22 | 29 |
| 23 | 62 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the data shown on Table III hereinabove, the compounds of the invention demonstrate significant affinity for the 5-HT6 receptor.

What is claimed is:

1. A compound of formula I

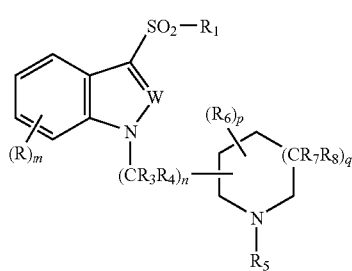

wherein
W is N;
R is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;

$R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1,2 or 3 additional heteroatoms selected from N, O or S;

$R_3$ and $R_4$ are each independently H or an optionally substituted $C_1$-$C_6$alkyl group;

$R_5$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted;

$R_6$ is a $C_1$-$C_6$alkyl, $C_3$-$C_7$cycloalkyl, $C_2$-$C_6$alkenyl or $C_2$-$C_6$alkynyl group each optionally substituted;

$R_7$ and $R_8$ are each independently H or a $C_1$-$C_6$alkyl, $C_3$-$C_7$cycloalkyl, $C_2$-$C_6$alkenyl or $C_2$-$C_6$alkynyl group each optionally substituted;

m, n and p are each independently 0 or an integer of 1, 2 or 3;

q and x are each independently 0 or an integer of 1 or 2;

$R_9$, $R_{10}$, $R_{13}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{11}$ and $R_{12}$ are each independently H or an optionally $C_1$-$C_6$alkyl group or $R_{11}$ and $R_{12}$ may be taken together with the atom to which they are attached to form a 5- to 7-member ring optionally containing another heteroatom selected from O, N or S;

$R_{14}$ and $R_{15}$ are each independently H or an optionally substituted $C_1$-$C_4$alkyl group or $R_{14}$ and $R_{15}$ may be taken together with the atom to which they are attached to form a 5- to 7-membered ring optionally containing another heteroatom selected from O, $NR_{18}$ or $SO_x$;

$R_{16}$ is a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; and $R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; or the stereoisomers thereof or the pharmaceutically acceptable salts thereof.

2. The compound according to claim 1 wherein n is 0 or 1.

3. The compound according to claim 1 wherein $R_5$ is H.

4. The compound according to claim 1 wherein $R_1$ is an optionally substituted phenyl group.

5. The compound according to claim 2 wherein q is 0 or 1.

6. The compound according to claim 2 wherein m is 0 and p is 0.

7. The compound according to claim 5 wherein the piperidinyl or pyrrolidinyl group is attached in the 3-position.

8. The compound according to claim 6 wherein $R_1$ is an optionally substituted phenyl group and q is 0 or 1.

9. A pharmaceutical composition which comprises a pharmaceutically acceptable carrier and an effective amount of a compound of formula I

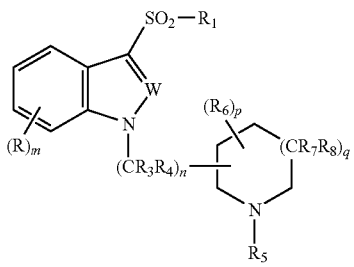

(I)

wherein
W is N;
R is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;
$R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1,2 or 3 additional heteroatoms selected from N, O or S;
$R_3$ and $R_4$ are each independently H or an optionally substituted $C_1$-$C_6$alkyl group;
$R_5$ is H or a $C_1$-$C_6$alkyl, $C_2$-$C_6$alkenyl, $C_2$-$C_6$alkynyi, $C_3$-$C_7$cycloalkyl, cycloheteroalkyl, aryl or heteroaryl group each optionally substituted;
$R_6$ is a $C_1$-$C_6$alkyl, $C_3$-$C_7$cycloalkyl, $C_2$-$C_6$alkenyl or $C_2$-$C_6$alkynyl group each optionally substituted;
$R_7$ and $R_8$ are each independently H or a $C_1$-$C_6$alkyl, $C_3$-$C_7$cycloalkyl, $C_2$-$C_6$alkenyl or $C_2$-$C_6$alkynyl group each optionally substituted;
m, n and p are each independently 0 or an integer of 1,2 or 3;
q and x are each independently 0 or an integer of 1 or 2;
$R_9$, $R_{10}$, $R_{13}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{11}$ and $R_{12}$ are each independently H or an optionally $C_1$-$C_6$alkyl group or $R_{11}$ and $R_{12}$ may be taken together with the atom to which they are attached to form a 5- to 7-member ring optionally containing another heteroatom selected from O, N or S;
$R_{14}$ and $R_{15}$ are each independently H or an optionally substituted $C_1$-$C_4$alkyl group or $R_{14}$ and $R_{15}$ may be taken together with the atom to which they are attached to form a 5- to 7-membered ring optionally containinq another heteroatom selected from O, $NR_{18}$ or $SO_x$;
$R_{16}$ is a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; and
$R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; or
the stereoisomers thereof or the pharmaceutically acceptable salts thereof.

10. The composition according to claim 9 having a formula I compound wherein n is 0 or 1.

11. The composition according to claim 10 having a formula I compound wherein $R_5$ is H and q is 0 or 1.

12. The composition according to claim 11 having a formula I compound wherein $R_1$ is an optionally substituted phenyl group.

13. The composition according to claim 12 having a formula I compound wherein the piperidinyl or pyrrolidinyl group is attached in the 3-position.

14. A process for the preparation of a compound of formula I

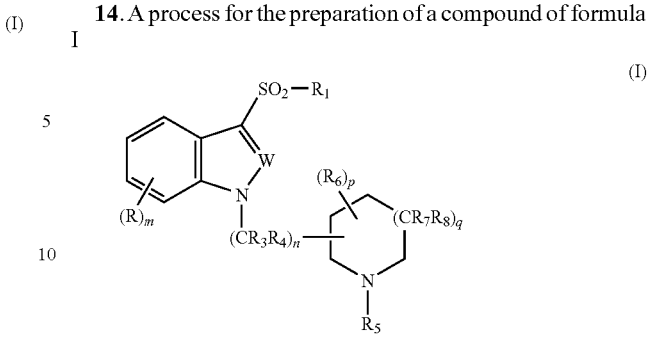

(I)

wherein
W is N;
R is halogen, CN, $OCO_2R_9$, $CO_2R_{10}$, $CONR_{11}R_{12}$, $SO_xR_{13}$, $NR_{14}R_{15}$, $OR_{16}$, $COR_{17}$ or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;
$R_1$ is an optionally substituted $C_1$-$C_6$alkyl, $C_3$-$C_7$cycloalkyl, aryl, or heteroaryl group or an optionally substituted 8- to 13-membered bicyclic or tricyclic ring system having a N atom at the bridgehead and optionally containing 1,2 or 3 additional heteroatoms selected from N, O or S;
$R_3$ and $R_4$ are each independently H or an optionally substituted $C_1$-$C_6$alkyl group;
$R_5$ is H or a $C_1$-$C_6$alkyl, $C_2$-$C_6$alkenyl, $C_2$-$C_6$alkynyi, $C_3$-$C_7$cycloalkyl, cycloheteroalkyl, aryl or heteroaryl group each optionally substituted;
$R_6$ is a $C_1$-$C_6$alkyl, $C_3$-$C_7$cycloalkyl, $C_2$-$C_6$alkenyl or $C_2$-$C_6$alkynyl group each optionally substituted;
$R_7$ and $R_8$ are each independently H or a $C_1$-$C_6$alkyl, $C_3$-$C_7$cycloalkyl, $C_2$-$C_6$alkenyl or $C_2$-$C_6$alkynyl group each optionally substituted;
m, n and p are each independently 0 or an integer of 1,2 or 3;
q and x are each independently 0 or an integer of 1 or 2;
$R_9$, $R_{10}$, $R_{13}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{11}$ and $R_{12}$ are each independently H or an optionally $C_1$-$C_6$alkyl group or $R_{11}$ and $R_{12}$ may be taken together with the atom to which they are attached to form a 5- to 7-member ring optionally containing another heteroatom selected from O, N or S;
$R_{14}$ and $R_{15}$ are each independently H or an optionally substituted $C_1$-$C_4$alkyl group or $R_{14}$ and $R_{15}$ may be taken together with the atom to which they are attached to form a 5- to 7-membered ring optionally containinq another heteroatom selected from O, $NR_{18}$ or $SO_x$;
$R_{16}$ is a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; and
$R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted
which process comprises reacting a compound of formula VIII

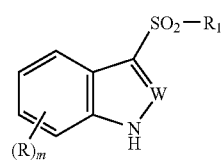

(VIII)

wherein W, R, $R_1$ and m are as described hereinabove with a protected azacyclic compound of formula IX

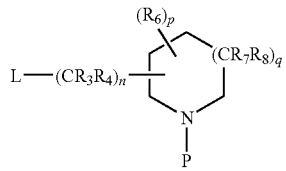

(IX)

wherein P is a protecting group; L is a leaving group; and $R_3$, $R_4$, $R_6$, $R_7$, $R_8$, n, p and q are as described hereinabove in the presence of a first base to give the protected formula I compound; and deprotecting said compound to give the free amine of formula I wherein $R_5$ is H optionally alkylating said amine with an alkylating agent, $R_5$-L', wherein L' is a leaving group in the presence of a second base.

* * * * *